(12) United States Patent
Palti et al.

(10) Patent No.: US 11,918,383 B2
(45) Date of Patent: Mar. 5, 2024

(54) VISUALIZING PERFORMANCE OF CATHETER ELECTRODES

(71) Applicant: Biosense Webster (Israel) Ltd., Yoknear (IL)

(72) Inventors: Yair Palti, Herzelia (IL); Vadim Gliner, Haifa (IL); Assaf Govari, Haifa (IL); Israel Zilberman, Yokneam (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 255 days.

(21) Appl. No.: 17/129,687

(22) Filed: Dec. 21, 2020

(65) Prior Publication Data

US 2022/0192604 A1 Jun. 23, 2022

(51) Int. Cl.
*A61B 5/00* (2006.01)
*A61B 5/287* (2021.01)
(Continued)

(52) U.S. Cl.
CPC ............ *A61B 5/7221* (2013.01); *A61B 5/287* (2021.01); *A61B 5/339* (2021.01); *A61B 5/346* (2021.01);
(Continued)

(58) Field of Classification Search
CPC ....... A61B 5/7221; A61B 5/346; A61B 5/339; A61B 5/367; A61B 5/287; A61B 5/6858; A61B 5/6885; A61B 5/7264; A61B 5/7267; A61B 5/7435; A61B 2562/0209; A61B 5/316; A61B 5/347; A61B 5/343;
(Continued)

(56) References Cited

U.S. PATENT DOCUMENTS 4,699,147 A 10/1987 Chilson et al.
4,940,064 A 7/1990 Desai
(Continued)

FOREIGN PATENT DOCUMENTS

CN 111248993 A 6/2020
CN 111248996 A 6/2020
(Continued)

OTHER PUBLICATIONS

Extended European Search Report dated Mar. 22, 2022, from corresponding EP Appl. No. 21215801.8.
(Continued)

*Primary Examiner* — Ronald Hupczey, Jr.
*Assistant Examiner* — Abigail Bock
(74) *Attorney, Agent, or Firm* — Troutman Pepper Hamilton Sanders LLP

(57) ABSTRACT

A system for electrophysiological measurement includes a probe having a distal end configured for insertion into a body cavity of a living subject and including an array of electrodes that are disposed along the distal end and are configured to contact tissue at multiple locations within the body cavity. A processor is configured to acquire signals from the electrodes over a period of time during which the probe moves within the body cavity, to compute, in response the signals, metrics that are indicative of a respective quality of contact between each of the electrodes and the tissue over the period of time, and to output an indication of the metrics to a user of the system.

16 Claims, 2 Drawing Sheets

(51) Int. Cl.
  *A61B 5/339* (2021.01)
  *A61B 5/346* (2021.01)
  *A61B 5/367* (2021.01)
  *G16H 20/40* (2018.01)
  *G16H 40/63* (2018.01)

(52) U.S. Cl.
  CPC ............ *A61B 5/367* (2021.01); *A61B 5/6858* (2013.01); *A61B 5/6885* (2013.01); *A61B 5/7264* (2013.01); *G16H 20/40* (2018.01); *G16H 40/63* (2018.01); *A61B 5/7267* (2013.01); *A61B 5/7435* (2013.01); *A61B 2562/0209* (2013.01)

(58) Field of Classification Search
  CPC ........... A61B 5/25; A61B 5/252; A61B 5/259; A61B 5/274; A61B 5/276; G16H 20/40; G16H 40/63
  See application file for complete search history.

(56) References Cited

U.S. PATENT DOCUMENTS

| | | |
|---|---|---|
| 5,215,103 A | 6/1993 | Desai |
| 5,255,679 A | 10/1993 | Imran |
| 5,293,869 A | 3/1994 | Edwards et al. |
| 5,309,910 A | 5/1994 | Edwards et al. |
| 5,313,943 A | 5/1994 | Houser et al. |
| 5,324,284 A | 6/1994 | Imran |
| 5,345,936 A | 9/1994 | Pomeranz et al. |
| 5,365,926 A | 11/1994 | Desai |
| 5,396,887 A | 3/1995 | Imran |
| 5,400,783 A | 3/1995 | Pomeranz et al. |
| 5,411,025 A | 5/1995 | Webster, Jr. |
| 5,415,166 A | 5/1995 | Imran |
| 5,456,254 A | 10/1995 | Pietroski et al. |
| 5,465,717 A | 11/1995 | Imran et al. |
| 5,476,495 A | 12/1995 | Kordis et al. |
| 5,499,981 A | 3/1996 | Kordis |
| 5,526,810 A | 6/1996 | Wang |
| 5,546,940 A | 8/1996 | Panescu et al. |
| 5,549,108 A | 8/1996 | Edwards et al. |
| 5,558,073 A | 9/1996 | Pomeranz et al. |
| 5,577,509 A | 11/1996 | Panescu et al. |
| 5,595,183 A | 1/1997 | Swanson et al. |
| 5,598,848 A | 2/1997 | Swanson et al. |
| 5,609,157 A | 3/1997 | Panescu et al. |
| 5,628,313 A | 5/1997 | Webster, Jr. |
| 5,681,280 A | 10/1997 | Rusk et al. |
| 5,722,401 A | 3/1998 | Pietroski et al. |
| 5,722,403 A | 3/1998 | McGee et al. |
| 5,725,525 A | 3/1998 | Kordis |
| 5,730,128 A | 3/1998 | Pomeranz et al. |
| 5,772,590 A | 6/1998 | Webster, Jr. |
| 5,782,899 A | 7/1998 | Imran |
| 5,823,189 A | 10/1998 | Kordis |
| 5,881,727 A | 3/1999 | Edwards |
| 5,893,847 A | 4/1999 | Kordis |
| 5,904,680 A | 5/1999 | Kordis et al. |
| 5,911,739 A | 6/1999 | Kordis et al. |
| 5,928,228 A | 7/1999 | Kordis et al. |
| 5,968,040 A | 10/1999 | Swanson et al. |
| 6,014,579 A | 1/2000 | Pomeranz et al. |
| 6,014,590 A | 1/2000 | Whayne et al. |
| 6,119,030 A | 9/2000 | Morency |
| 6,216,043 B1 | 4/2001 | Swanson et al. |
| 6,216,044 B1 | 4/2001 | Kordis |
| 6,428,537 B1 | 8/2002 | Swanson et al. |
| 6,456,864 B1 | 9/2002 | Swanson et al. |
| 6,574,492 B1 | 6/2003 | Ben-Haim et al. |
| 6,584,345 B2 | 6/2003 | Govari |
| 6,600,948 B2 | 7/2003 | Ben-Haim et al. |
| 6,738,655 B1 | 5/2004 | Sen et al. |
| 6,741,878 B2 | 5/2004 | Fuimaono et al. |
| 6,748,255 B2 | 6/2004 | Fuimaono et al. |
| 6,780,183 B2 | 8/2004 | Jimenez, Jr. et al. |
| 6,837,886 B2 | 1/2005 | Collins et al. |
| 6,866,662 B2 | 3/2005 | Fuimaono et al. |
| 6,892,091 B1 | 5/2005 | Ben-Haim et al. |
| 6,970,730 B2 | 11/2005 | Fuimaono et al. |
| 6,973,340 B2 | 12/2005 | Fuimaono et al. |
| 6,980,858 B2 | 12/2005 | Fuimaono et al. |
| 7,048,734 B1 | 5/2006 | Fleischman et al. |
| 7,149,563 B2 | 12/2006 | Fuimaono et al. |
| 7,255,695 B2 | 8/2007 | Falwell et al. |
| 7,257,434 B2 | 8/2007 | Fuimaono et al. |
| 7,399,299 B2 | 7/2008 | Daniel et al. |
| 7,410,486 B2 | 8/2008 | Fuimaono et al. |
| 7,522,950 B2 | 4/2009 | Fuimaono et al. |
| RE41,334 E | 5/2010 | Beatty et al. |
| 7,846,157 B2 | 12/2010 | Kozel |
| 7,930,018 B2 | 4/2011 | Harlev et al. |
| 8,007,495 B2 | 8/2011 | McDaniel et al. |
| 8,048,063 B2 | 11/2011 | Aeby et al. |
| 8,103,327 B2 | 1/2012 | Harlev et al. |
| 8,167,845 B2 | 5/2012 | Wang et al. |
| 8,224,416 B2 | 7/2012 | De La Rama et al. |
| 8,235,988 B2 | 8/2012 | Davis et al. |
| 8,346,339 B2 | 1/2013 | Kordis et al. |
| 8,435,232 B2 | 5/2013 | Aeby et al. |
| 8,447,377 B2 | 5/2013 | Harlev et al. |
| 8,498,686 B2 | 7/2013 | Grunewald |
| 8,517,999 B2 | 8/2013 | Pappone et al. |
| 8,545,490 B2 | 10/2013 | Mihajlovic et al. |
| 8,560,086 B2 | 10/2013 | Just et al. |
| 8,567,265 B2 | 10/2013 | Aeby et al. |
| 8,712,550 B2 | 4/2014 | Grunewald |
| 8,755,861 B2 | 6/2014 | Harlev et al. |
| 8,825,130 B2 | 9/2014 | Just et al. |
| 8,906,011 B2 | 12/2014 | Gelbart et al. |
| 8,945,120 B2 | 2/2015 | McDaniel et al. |
| 8,979,839 B2 | 3/2015 | De La Rama et al. |
| 9,037,264 B2 | 5/2015 | Just et al. |
| 9,131,980 B2 | 9/2015 | Bloom |
| 9,168,004 B2 | 10/2015 | Gliner et al. |
| 9,204,929 B2 | 12/2015 | Solis |
| 9,277,960 B2 | 3/2016 | Weinkam et al. |
| 9,314,208 B1 | 4/2016 | Altmann et al. |
| 9,339,331 B2 | 5/2016 | Tegg et al. |
| 9,486,282 B2 | 11/2016 | Solis |
| 9,554,718 B2 | 1/2017 | Bar-Tal et al. |
| D782,686 S | 3/2017 | Werneth et al. |
| 9,585,588 B2 | 3/2017 | Marecki et al. |
| 9,597,036 B2 | 3/2017 | Aeby et al. |
| 9,687,297 B2 | 6/2017 | Just et al. |
| 9,693,733 B2 | 7/2017 | Altmann et al. |
| 9,782,099 B2 | 10/2017 | Williams et al. |
| 9,788,895 B2 | 10/2017 | Solis |
| 9,801,681 B2 | 10/2017 | Laske et al. |
| 9,814,618 B2 | 11/2017 | Nguyen et al. |
| 9,833,161 B2 | 12/2017 | Govari |
| 9,894,756 B2 | 2/2018 | Weinkam et al. |
| 9,895,073 B2 | 2/2018 | Solis |
| 9,907,609 B2 | 3/2018 | Cao et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,231,328 B2 | 3/2019 | Weinkam et al. |

(56) References Cited

U.S. PATENT DOCUMENTS

| | | |
|---|---|---|
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,872 B2 | 3/2020 | Severino |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,317 B2 | 4/2020 | Cohen et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2004/0210121 A1 | 10/2004 | Fuimaono et al. |
| 2006/0009689 A1 | 1/2006 | Fuimaono et al. |
| 2006/0009690 A1 | 1/2006 | Fuimaono et al. |
| 2006/0100669 A1 | 5/2006 | Fuimaono et al. |
| 2007/0093806 A1 | 4/2007 | Desai et al. |
| 2007/0276212 A1 | 11/2007 | Fuimaono et al. |
| 2008/0234564 A1 | 9/2008 | Beatty et al. |
| 2011/0118726 A1 | 5/2011 | De La Rama et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0296852 A1 | 11/2013 | Madjarov et al. |
| 2014/0025069 A1 | 1/2014 | Willard et al. |
| 2014/0052118 A1 | 2/2014 | Laske et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0257069 A1 | 9/2014 | Eliason et al. |
| 2014/0276712 A1 | 9/2014 | Mallin et al. |
| 2014/0309512 A1 | 10/2014 | Govari et al. |
| 2015/0011991 A1 | 1/2015 | Buysman et al. |
| 2015/0045863 A1 | 2/2015 | Litscher et al. |
| 2015/0080693 A1 | 3/2015 | Solis |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0208942 A1 | 7/2015 | Bar-Tal et al. |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2016/0008065 A1 | 1/2016 | Gliner et al. |
| 2016/0081746 A1 | 3/2016 | Solis |
| 2016/0113582 A1 | 4/2016 | Altmann et al. |
| 2016/0113709 A1 | 4/2016 | Maor |
| 2016/0183877 A1 | 6/2016 | Williams et al. |
| 2016/0228023 A1 | 8/2016 | Govari |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2017/0027638 A1 | 2/2017 | Solis |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0156790 A1 | 6/2017 | Aujla |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0049803 A1 | 2/2018 | Solis |
| 2018/0085064 A1 | 3/2018 | Auerbach et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0242868 A1* | 8/2018 | Cohen ............... A61B 5/743 |
| 2018/0249691 A1 | 9/2018 | Osypka |
| 2018/0256109 A1 | 9/2018 | Wu et al. |
| 2018/0279954 A1 | 10/2018 | Hayam et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |

(56) References Cited

U.S. PATENT DOCUMENTS

| | | |
|---|---|---|
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0183378 A1 | 6/2019 | Mosesov et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0367829 A1 | 11/2020 | Govari et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0169421 A1 | 6/2021 | Govari |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0200412 A1* | 7/2021 | Cao .................. H01Q 1/22 |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |
| 2022/0047220 A1 | 2/2022 | Palti et al. |

FOREIGN PATENT DOCUMENTS

| | | |
|---|---|---|
| EP | 0668740 A1 | 8/1995 |
| EP | 0644738 B1 | 3/2000 |
| EP | 0727183 B1 | 11/2002 |
| EP | 0727184 B1 | 12/2002 |
| EP | 2783651 A1 | 10/2014 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3238645 A1 | 11/2017 |
| EP | 2884931 B1 | 1/2018 |
| EP | 2349440 B1 | 8/2019 |
| EP | 3318211 B1 | 12/2019 |
| EP | 3581135 A1 | 12/2019 |
| EP | 2736434 B1 | 2/2020 |
| EP | 3451962 B1 | 3/2020 |
| EP | 3972510 A1 | 3/2022 |
| WO | 9421167 A1 | 9/1994 |
| WO | 9421169 A1 | 9/1994 |
| WO | 9625095 A1 | 8/1996 |
| WO | 9634560 A1 | 11/1996 |
| WO | 0182814 B1 | 5/2002 |
| WO | 2004087249 A2 | 10/2004 |
| WO | 2012100185 A2 | 7/2012 |
| WO | 2013052852 A1 | 4/2013 |
| WO | 2013162884 A1 | 10/2013 |
| WO | 2013173917 A1 | 11/2013 |
| WO | 2013176881 A1 | 11/2013 |
| WO | 2014176205 A1 | 10/2014 |
| WO | 2016019760 A1 | 2/2016 |
| WO | 2016044687 A1 | 3/2016 |
| WO | 2018111600 A1 | 6/2018 |
| WO | 2018191149 A1 | 10/2018 |
| WO | 2019084442 A1 | 5/2019 |
| WO | 2019143960 A1 | 7/2019 |

(56) References Cited

FOREIGN PATENT DOCUMENTS

| WO | 2020026217 A1 | 2/2020 |
| WO | 2020206328 A1 | 10/2020 |

OTHER PUBLICATIONS

European Search Report dated Mar. 30, 2023, from corresponding European Application No. 21215801.8.

* cited by examiner

VISUALIZING PERFORMANCE OF CATHETER ELECTRODES

FIELD OF THE INVENTION

The present invention relates generally to apparatus and methods for sensing and mapping of electrophysiological (EP) signals, and particularly to methods for evaluating the operation of such apparatus.

BACKGROUND

In cardiac electroanatomical mapping systems that are known in the art, an operator—typically a physician—inserts a catheter through a patient's vascular system into a chamber of the heart. An electrode or electrode assembly at the distal end of the catheter contacts the myocardial tissue in the chamber and receives electrical signals from the tissue, which are conveyed through the catheter to a mapping console. The operator manipulates the catheter within the heart in order to acquire signals from many points within the heart chamber, thus enabling the console to construct a map showing the physical structure of the walls of the heart chamber and the distribution of electrical activity over the walls.

As the operator cannot see the distal end of the catheter in the heart chamber, a number of techniques have been developed to assist the operator in visualizing and understanding the process of EP signal acquisition. For example, U.S. Pat. No. 10,617,317 describes a method for highlighting an electrode image according to an electrode signal. A graphical image of a heart of a patient is presented on a display screen, including icons representing a catheter that is positioned within the heart and an electrode on the catheter, while the electrode is in contact with tissue at a location in the heart. The method further includes acquiring, using the electrode, electrical signals from the tissue at the location, and processing the acquired signals so as to detect an occurrence of a predefined signal feature in the acquired signals. The method also includes, upon detecting the occurrence of the predefined signal feature, modifying a visual feature of at least one of the icon representing the electrode and the icon representing the catheter on the display screen.

As another example, U.S. Pat. No. 10,582,872 describes a method and system for visualization of electrophysiology information sensed by electrodes on a catheter. The method includes recording times of electrode signal acquisition, designating a reference electrode signal acquisition, assigning a relative time to each recorded time of electrode signal acquisition relative to the reference electrode signal acquisition, identifying the electrodes with signal acquisition, correlating assigned relative times to identified electrodes to generate a sequence of electrode signal acquisitions, and generating a visual representation of the sequence of electrode signal acquisitions generating a visual representation with a graphical image of the electrodes, wherein individual electrodes are visually marked to represent the sequence of electrode signal acquisitions.

SUMMARY

Embodiments of the present invention that are described hereinbelow provide improved methods and systems for visualization of EP signal acquisition.

There is therefore provided, in accordance with an embodiment of the invention, a system for electrophysiological measurement, including a probe having a distal end configured for insertion into a body cavity of a living subject and including an array of electrodes that are disposed along the distal end and are configured to contact tissue at multiple locations within the body cavity. A processor is configured to acquire signals from the electrodes over a period of time during which the probe moves within the body cavity, to compute, in response the signals, metrics that are indicative of a respective quality of contact between each of the electrodes and the tissue over the period of time, and to output an indication of the metrics to a user of the system.

In a disclosed embodiment, the probe includes a catheter, and the distal end is configured for insertion into a chamber of a heart of the living subject.

Additionally or alternatively, the distal end of the probe includes a flexible structure on which the electrodes are arrayed, and the metrics are indicative of a contact between different parts of the flexible structure and the tissue. In some embodiments, the structure includes multiple flexible spines along which the electrodes are disposed.

In some embodiments, the processor is configured to render to a display a graphical icon representing the distal end and to incorporate in the graphical icon visual indications of the metrics at respective locations of the electrodes on the distal end. In a disclosed embodiment, the metrics are represented by color-coding of the respective locations of the electrodes on the graphical icon.

In one embodiment, the metrics are indicative of a number of valid signals acquired by each of the electrodes from the tissue over the period of time. Typically, the processor is configured to apply one or more filtering criteria to the signals in order to classify as valid a respective first set of the signals acquired from each of the electrodes while classifying as invalid a respective second set of the signals acquired by each of the electrodes.

In other embodiments, the metrics are indicative of a respective duration during which each of the electrodes was in contact with the tissue in the body cavity over the period of time. In one such embodiment, the signals are indicative of an electrophysiological activity within the tissue, and the processor is configured to distinguish between local signals acquired by the electrodes that are in contact with the tissue and far-field signals acquired by the electrodes that are not in contact with the tissue, and to find the duration during which each of the electrodes is in contact with the tissue in response a relation between the local and far-field signals acquired by each of the electrodes over the period of time.

There is also provided, in accordance with an embodiment of the invention, a method for electrophysiological measurement, which includes inserting into a body cavity of a living subject a probe having a distal end including an array of electrodes that are disposed along the distal end and are configured to contact tissue at multiple locations within the body cavity. Signals are acquired from the electrodes within the body cavity over a period of time during which the probe moves within the body cavity. Responsively to the signals, metrics are computed, wherein the metrics are indicative of a respective quality of contact between each of the electrodes and the tissue over the period of time. An indication of the metrics is outputted to a user of the system.

The present invention will be more fully understood from the following detailed description of the embodiments thereof, taken together with the drawings in which:

DETAILED DESCRIPTION OF EMBODIMENTS

Overview

Figure 1:
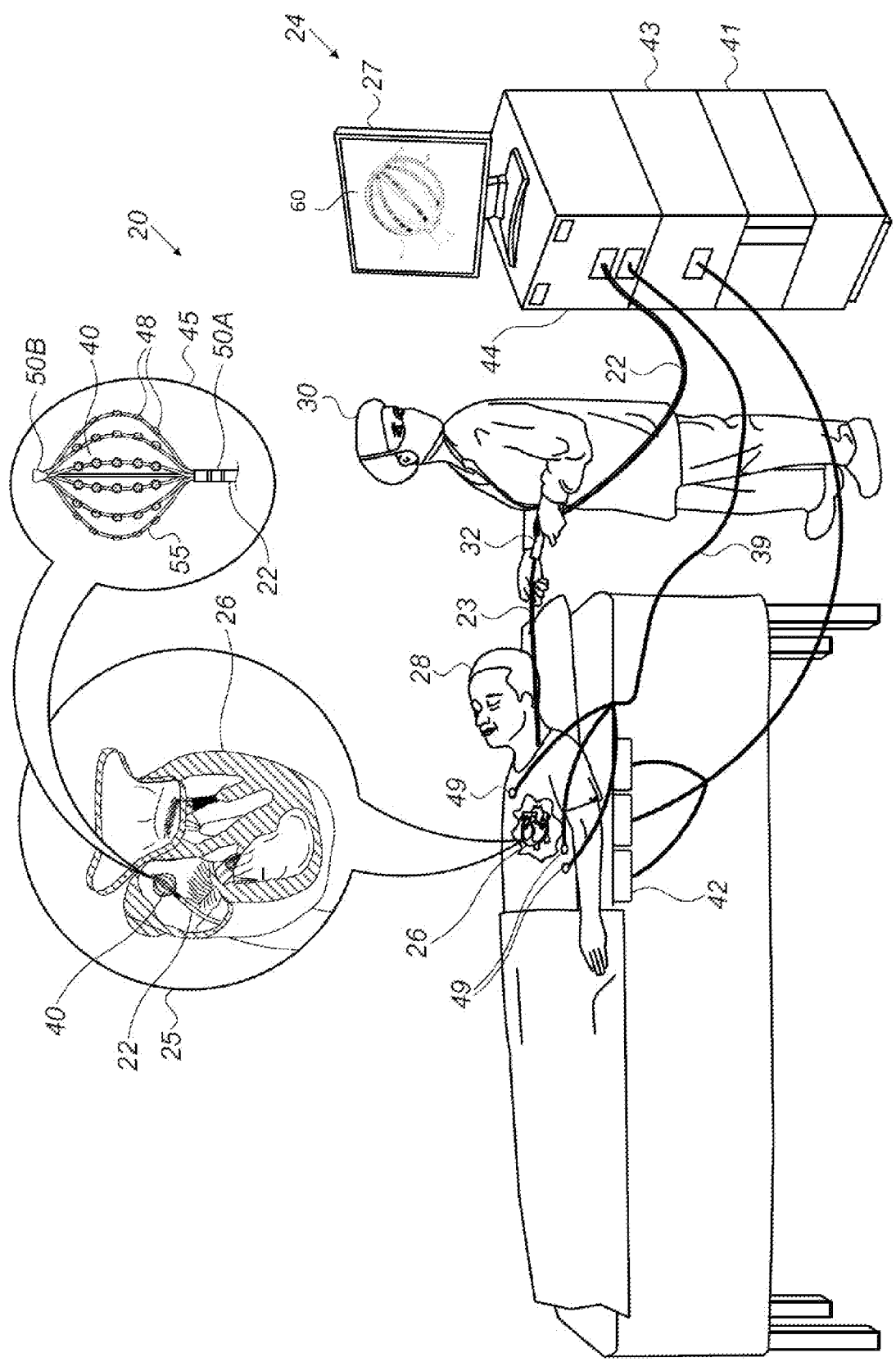
FIG. 1 is a schematic pictorial illustration of a system for electroanatomical mapping, in accordance with an embodiment of the present invention.

To produce an accurate electroanatomical map of a heart chamber, a mapping system typically acquires electrical signals from hundreds or even thousands of different points along the wall of the chamber. To reduce the time needed to acquire this large volume of data, mapping systems commonly use catheters having many electrodes at their distal ends, which are capable of sensing respective signals simultaneously at different, respective locations within the heart chamber. The electrodes are typically arrayed along a flexible structure at the distal end of the catheter, such as a balloon or a structure with multiple flexible spines along which the electrodes are disposed, such as a basket or a multi-arm assembly.

In typical operation, not all of the electrodes will be in contact with the tissue at any given time. The signal received by a catheter electrode that is not in contact with tissue in the heart is generally dominated by the far-field signal transmitted through the blood pool in which the electrode is immersed. This far-field component is of limited diagnostic value. When the catheter electrode is in contact with the heart tissue, the amplitude of the signal derives mainly from local tissue conductivity, while the far-field contribution is minor.

Thus, for efficient, accurate EP measurement and mapping, it is generally desirable that as many electrodes as possible make contact with the tissue at all times during the procedure, and that the contact be of good quality so that the signals are suitable for incorporation in the map. By the same token, when a new catheter is in development, it is important to the designer to understand how well each of the electrodes is performing in terms of consistency of tissue contact in order to optimize the distal structure of the catheter and the placement of the electrodes on this structure. Although it is possible to evaluate the performance of any single electrode by observing the signals that it collects, the volume of data provided by the signals from the entire array of electrodes at any given time is far too large for the operator or designer to digest. It is thus difficult, for example, for the designer to assess which of the electrodes make consistently good contact with the tissue as the catheter moves through the heart chamber and which do not, in order to improve the design to achieve better, more consistent contact. There is a need for automated tools that can provide this sort of assessment and assist developers and users of catheters in improving their design and operating technique.

Embodiments of the present invention that are described here address this problem by providing a visual indication of the performance of each of the electrodes in the electrode array at the distal end of a probe, such as a catheter, in a system for electrophysiological measurement. To generate this indication, a processor acquires signals from the electrodes as the probe moves within a body cavity, such as a heart chamber. Based on the acquired signals, the processor continually evaluates the quality of contact between each electrode and the tissue in the cavity wall. For this purpose, for instance, the processor may process the signals that it acquires from each electrode in order to distinguish between local signals and far-field signals or to measure impedance though the electrodes.

For each electrode, the processor then computes a metric indicative of the quality of contact between the electrode and the tissue over a period of time during which the probe moved within the body cavity. The metric may indicate, for example, the number of valid signals acquired by each of the electrodes from the tissue over the period of time. For this purpose, for example, the processor may apply filtering criteria to the signals in order to classify the signals that meet the criteria as valid, while classifying as invalid signals that do not meet the criteria and should therefore be discarded. Methods and criteria for performing this sort of filtering are described, for example, in U.S. patent application Ser. No. 16/995,036, filed Aug. 17, 2020, which is assigned to the assignee of the present patent application and is incorporated herein by reference with a copy attached to the Appendix. Additionally or alternatively, the metric may indicate the duration during which each of the electrodes was found to be in contact with the tissue over the period of time.

The processor outputs an indication of the metrics to a user of the system. In the embodiments described below, the indication takes the form of a graphical icon representing the distal end of the probe, which the processor renders to a display. The icon includes visual indications of the metrics at the locations of the electrodes on the distal end of the probe, for example by color-coding the electrode locations on the display. This icon and/or other output enables an operator or designer to visualize the effectiveness of each of the electrodes in contacting the tissue and thus to improve either the probe design or the operating technique, as the case may be, in order to optimize the efficiency of data collection and mapping. For example, the designer may eliminate electrodes that had poor quality of contact and/or may concentrate the electrodes in areas of the probe that had good quality of contact in order to maximize the collection of valid signals relative to the available area and to the number of signal wires in the probe.

For the sake of concreteness and clarity, the embodiments that are shown in the figures and described below relate, by way of example, to a particular type of system for electroanatomical mapping and a basket catheter that can be used in such a system. The principles of the present invention, however, are by no means limited to this particular sort of catheter or system, and may similarly be applied, mutatis mutandis, to cardiac catheters of other types for diagnostic and therapeutic applications, as well as to probes used for diagnostic measurements and treatment in other body cavities. All such alternative implementations are considered to be within the scope of the present invention.

System Description

FIG. 1 is a schematic pictorial illustration of a system 20 for mapping an EP parameter in a heart 26 of a patient 28, in accordance with an embodiment of the present invention. The embodiment shown in the current figure and subsequent figures refers to an example of acquiring EP signals from a chamber of heart 26. In alternative embodiments, the values of EP parameters may be acquired using other sorts of mapping apparatus, not only from within the heart, but also from other organs and tissue, as will be apparent to those skilled in the art after reading the present description.

An operator 30 navigates a catheter 22 to a target location in heart 26 of patient 28, by manipulating a shaft 23 of the catheter, using a manipulator 32 near the proximal end of the catheter. In the pictured example, catheter 22 comprises a basket assembly 40 at its distal end, as shown in an inset 45. As seen in an inset 25, operator 30 manipulates catheter 22 to perform electroanatomical mapping of a chamber of heart 26. EP signals are acquired from the myocardial tissue by bringing electrodes 48 on basket assembly 40 into contact with the tissue within the heart, as further detailed below.

In the pictured example, for purposes of position tracking, basket assembly 40 incorporates a pair of magnetic sensors 50A and 50B, seen in inset 45, at the proximal and distal ends of basket assembly 40. Alternatively, catheter 22 may comprise other sorts of magnetic sensors, at these or other locations. Alternatively or additionally, the catheter may comprise other sorts of position sensors, such as impedance-based or ultrasonic position sensors, as are known in the art.

Basket assembly 40 comprises multiple expandable spines 55, which are mechanically flexible. Multiple electrodes 48 are fixed to each spine, for a total of, for example, 120 electrodes. Electrodes 48 are configured to touch the tissue within heart 26 for the purpose of sensing EP signals, i.e., intracardiac electrogram signals in the pictured example. Magnetic sensors 50A and 50B and electrodes 48 are connected by wires (not shown) running through catheter 22 to processing circuits in a console 24.

Alternatively, system 20 may comprise other types of catheters, with other sorts of electrode arrays, such as an inflatable balloon catheter with electrodes 48 on its outer surface, or a catheter having one or more flexible arms or having a curved "lasso" at its distal end.

System 20 comprises a position-tracking sub-system 43 in console 24 for finding the position and orientation of basket assembly 40, and thereby identifying the locations of electrodes 48. Patient 28 is placed in a magnetic field generated by a pad containing magnetic field generator coils 42, which are driven by position-tracking sub-system 43. The magnetic fields generated by coils 42 give rise to electrical signals in sensors 50A and 50B, which are indicative of the position and orientation of the sensors. The signals from sensors 50A and 50B are transmitted back to position-tracking sub-system 43, which converts the signals to corresponding digital inputs to a processor 41. Processor 41 uses these inputs to compute the position and orientation of basket assembly 40 and thus to find the respective location coordinates of each of electrodes 48.

Alternatively or additionally, as noted above, system 20 may use other methods of position sensing to find the locations of electrodes 48. For example, processor 41 may map the locations of electrodes 48 by measuring impedances between electrodes 48 and body-surface electrodes 49, which are placed on the chest of patient 28 and connected to console 24 by leads 39.

Processor 41 additionally receives EP signals from electrodes 48 on basket assembly 40 via front-end circuits 44. These circuits apply analog and/or digital filters and amplifiers to the signals under the control of the processor. In a typical clinical application, processor uses the information contained in these EP signals together with the coordinates provided by magnetic sensors 50A and 50B in constructing an electroanatomical map of the chamber of heart 26 in which basket assembly 40 is located, such as a map showing the voltage levels or local activation time (LAT) of the EP signals as a function of location along the chamber walls. In the present embodiment, however, processor 41 renders a graphical icon 60 to a display 27, representing basket assembly 40. Icon 60 incorporates visual indications of the quality of contact of electrodes 48 at the respective locations of the electrodes on the basket assembly. Methods for computation of metrics that are indicative of the quality of contact and their incorporation in icon 60 are described below.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm that enables the processor to perform the disclosed steps of data acquisition, computation of quality of contact, and operator guidance, as described below.

As noted earlier, the example illustration shown in FIG. 1 is chosen purely for the sake of conceptual clarity. FIG. 1 shows only elements related to the disclosed techniques for the sake of simplicity and clarity. System 20 typically comprises additional modules and elements that are not directly related to the disclosed techniques, and thus are intentionally omitted from FIG. 1 and from the corresponding description.

Assessing and Displaying Quality of Contact

In response to signals provided by electrodes 48 on basket assembly 40, processor 41 assesses the respective quality of contact of each of the electrodes with the tissue in heart 26. Any one of electrodes 48 may be in full or partial contact with the tissue of the heart at any given time. Alternatively, any one of the electrodes may be separated from the tissue by a fluid, such as blood in the heart chamber, and will then receive signals from the tissue only through the fluid. The quality of contact (full or partial contact, or contact via fluid) of any one of the catheter electrodes with the tissue can be assessed based on the signals provided by the catheter. Based on these signals, processor 41 measures the quality of contact over a period during which basket assembly 40 moves within a chamber of the heart. The processor computes a metric for each electrode that is indicative of the quality of contact, for example as a function of the duration during which the electrode was in contact with the tissue over this period of time. In some embodiments, the metric for any given electrode corresponds to the number of valid signals acquired by the electrode during the period in question or to the fraction of the period during which there was good quality of contact between the electrode and the tissue.

The term "quality of contact," as used in the specification and claims, is defined as a quantitative indicator of the degree of stable electrical contact between any one of the catheter electrodes and the tissue. The "quality of contact" may be expressed directly, for example in terms of a measured electrical impedance, or indirectly, for example in terms of contact force or pressure, or based on the amplitude of the EP signals that are acquired by electrodes 48. Methods for assessing the quality of contact between multiple electrodes on a catheter and tissue in the heart are described in detail in U.S. Patent Application Publication 2020/0367829, which is assigned to the assignee of the present patent application and whose disclosure is incorporated herein by reference with a copy in the Appendix.

Additionally or alternatively, the quality of contact may be expressed in terms of the quality of signal acquisition through the electrodes, for example based on the number of signals acquired by each electrode 48 that are found to meet certain filtering criteria, such as the criteria described in the above-mentioned U.S. patent application Ser. No. 16/995,036. In one embodiment using this sort of quality metric, processor 41 acquires a signal from each electrode 48 in the heart chamber within a certain time window of interest during each heartbeat period. (The start time of the heartbeat period, known as a "reference annotation," is typically derived from the ECG signals received from body surface electrodes 49, and the window is defined relative to this reference annotation.) If the acquired signal and the electrode location during acquisition meet the filtering criteria, processor 41 counts the signal as valid and increments a count of the number of valid signals for this electrode. Otherwise, the signal is considered invalid and discarded. The contact quality metric for each electrode is based on the respective count.

By way of example, but not limitation, the filtering criteria used in counting the valid signals can include the following:

Proximity of electrodes to the wall of the heart chamber, for example based on the electrode location coordinates measure by the magnetic tracking system relative to the surface of the wall that has been reconstructed by a fast anatomical mapping (FAM) algorithm. Only the signals acquired at locations within a threshold distance of the wall are considered valid.

Catheter stability during acquisition. Processor 41 senses the extent and rate of motion of basket assembly 40 during acquisition of EP signals. When the basket assembly moves by more than a certain maximal distance during acquisition of an EP sample or set of samples, the processor will reject the signals as invalid.

Voltage too low. Processor 41 filters the EP signals by voltage level and will count as valid only the signals whose voltage was above a certain minimum.

Only signals meeting all of the above criteria are counted as valid. The thresholds (for wall proximity, stability, and voltage, inter alia) can be fixed, or they can be set by an operator of system 20.

In other embodiments, processor 41 measures the impedance between electrodes 48 and body surface electrodes 49. The magnitude of the impedance provides an indication of a quality of contact. Typically, a higher value of impedance between one of the electrodes and the body surface electrodes indicates a higher quality of contact between that catheter electrode and the tissue, whereas low impedance indicates that the electrode is immersed in the blood within the heart. Processor 41 may use the values of impedance in computing the metrics indicating the quality contact between each of the catheter electrodes and the tissue.

Alternatively or additionally, the impedance between pairs of electrodes 48 on basket 40 may be used as a measure of quality of contact. Tissue contact may be assessed by comparing impedance values across a set of electrodes to premeasured impedance values, including values measured for electrodes known to be in sufficient contact with tissue and other values for electrodes known to be in contact only with blood.

Further additionally or alternatively, machine learning techniques may be used in assessing the quality of contact between electrodes 48 and myocardial tissue, for example as described in U.S. Pat. No. 9,168,004, whose disclosure is incorporated herein by reference with a copy in the Appendix.

In some embodiments, the probe under evaluation may comprise force or pressure sensors (not shown in the figures). The measure of force or pressure provides an indication of a quality of contact, such that a higher value of force or pressure indicates a higher quality of contact between a corresponding electrode and the tissue, and vice versa.

In some embodiments, the EP signals acquired from electrodes 48 are used to assess the quality of contact between the electrodes and the tissue. Processor 41 distinguishes between local signals acquired when an electrode is in contact with the tissue and far-field signals acquired when the electrode is not in contact with the tissue, and finds the quality of contact based on the relation between the local and far-field signals. For example, the maximum amplitude (voltage) of the EP signal associated with any given electrode is indicative of the quality of contact between the electrode and the tissue, such that a higher value of the maximum amplitude of the EP signal indicates a higher quality of contact between that catheter electrode and the tissue. Processor 41 may use the amplitude of the EP signal in computing the metric indicating the quality of contact between each of the catheter electrodes and the tissue.

Alternatively or additionally, processor 41 may apply other methods for measuring the quality of contact between electrodes and tissue 48, such as the methods that are further described in the above-mentioned U.S. Patent Application Publication 2020/0367829 or other methods that are known in the art.

Figure 2:
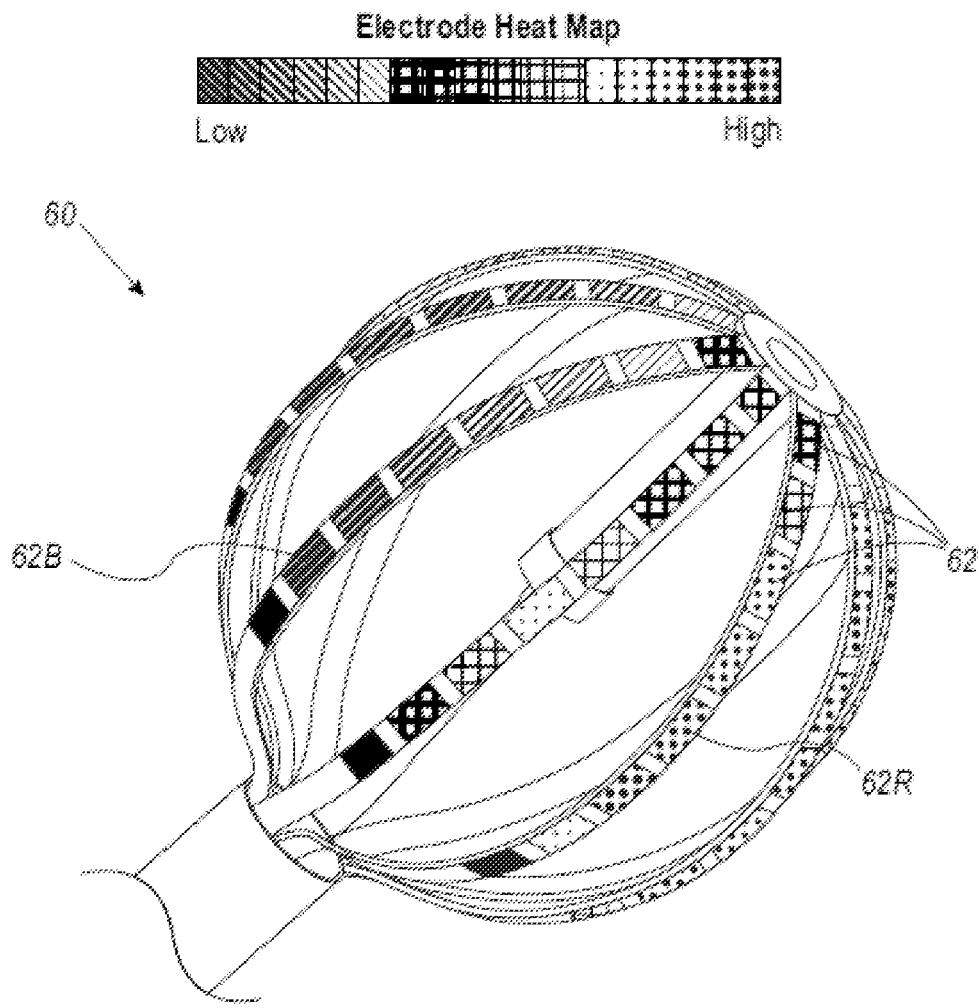
FIG. 2 is a schematic illustration of a graphical icon showing performance of electrodes on a catheter used in acquiring EP signals, in accordance with an embodiment of the present invention.
Figure 3:
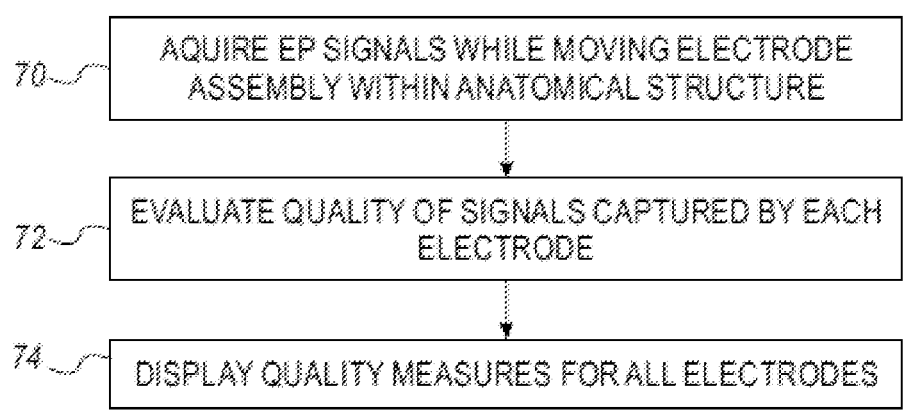
FIG. 3 is a flow chart that schematically illustrates a method for assessing and visualizing electrode performance, in accordance with an embodiment of the present invention.

Reference is now made to FIGS. 2 and 3, which schematically illustrate a method for assessing and visualizing electrode performance, in accordance with an embodiment of the present invention. FIG. 2 is a schematic illustration of graphical icon 60 showing the quality of contact of electrodes on a catheter used in acquiring EP signals, while FIG. 3 is a flow chart showing the method for computation and display of contact quality metrics. The method is described here with specific reference to catheter 22 as shown in FIG. 1; but it may alternative be applied, mutatis mutandis, to catheters of other types.

Processor 41 typically renders icon 60 to display 27 and superimposes markings 62 on icon 60 corresponding to the respective locations of electrodes 48 on spines 55. Markings 62 are color-coded to indicate the respective contact quality metrics of the corresponding electrodes, for example using a "heat" scale (represented by different hatch styles in FIG. 2), with blue indicating the least contact and red indicating the most. Thus, in the pictured example, a location 62B made relatively poor contact with the myocardial tissue, while another location 62R made good contact.

The color-coding of markings 62 shows by implication which of the spines or which parts of the spines made frequent contact with the myocardial tissue and which did not. The designer of catheter 22 can then change the shapes of the spines or the distribution of the electrodes thereon in order to optimize the design. The contact metrics may be different when the catheter is used in different chambers of the art; and the designer may accordingly develop different baskets and electrode layouts for different applications. By the same token, an operator of system 20 may use the color-coding on icon 60 to improve his or her mapping technique in order to capture EP data more effectively.

As the first step in creating and coloring icon 60, processor 41 collects data with respect to electrodes 48 while basket 40 moves within an anatomical structure, such as a chamber of the heart, at an acquisition step 70, as shown in FIG. 3. In the present example, the acquired data comprises EP signals sensed by the electrodes, although other sorts of data, such as impedance or pressure measurements, may be acquired alternatively or additionally. Processor 41 measures the quality of contact made by each electrode with the tissue and computes a corresponding metric, at a quality evaluation step 72.

Based on this evaluation, the processor outputs an indication of the contact quality metric for each electrode, at a quality display step 74. For example, electrode positions 62 on icon 60 may be colored according to the quality metrics as illustrated in FIG. 2. Alternatively or additionally, other sorts of graphical and/or numerical outputs may be used, as will be apparent to those skilled in the art after reading the present description.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A system for electrophysiological measurement, comprising:
    a probe having a distal end configured for insertion into a body cavity of a living subject and comprising an array of electrodes that are disposed along the distal end and are configured to contact tissue at multiple locations within the body cavity; and
    a processor configured to acquire signals from the electrodes over a period of time during which the probe moves within the body cavity, to compute, in response to the signals, metrics that are indicative of a respective quality of contact between each of the electrodes and the tissue over the period of time, each respective quality of contact being a quantitative indicator of a degree of stable electrical contact between each of the electrodes and the tissue, and to output an indication of the metrics to a user of the system,
    wherein the metrics are indicative of a respective duration during which each of the electrodes was in contact with the tissue in the body cavity over the period of time,
    wherein the signals are indicative of an electrophysiological activity within the tissue, and wherein the processor is configured to distinguish between local signals acquired by the electrodes that are in contact with the tissue and far-field signals acquired by the electrodes that are not in contact with the tissue, and to find the duration during which each of the electrodes is in contact with the tissue in response a relation between the local and far-field signals acquired by each of the electrodes over the period of time.

2. The system according to claim 1, wherein the probe comprises a catheter, and the distal end is configured for insertion into a chamber of a heart of the living subject.

3. The system according to claim 1, wherein the distal end of the probe comprises a flexible structure on which the electrodes are arrayed, and the metrics are indicative of a contact between different parts of the flexible structure and the tissue.

4. The system according to claim 3, wherein the structure comprises multiple flexible spines along which the electrodes are disposed.

5. The system according to claim 1, wherein the processor is configured to render to a display a graphical icon representing the distal end and to incorporate in the graphical icon visual indications of the metrics at respective locations of the electrodes on the distal end.

6. The system according to claim 5, wherein the metrics are represented by color-coding of the respective locations of the electrodes on the graphical icon.

7. The system according to claim 1, wherein the metrics are indicative of a number of valid signals acquired by each of the electrodes from the tissue over the period of time.

8. The system according to claim 7, wherein the processor is configured to apply one or more filtering criteria to the signals in order to classify as valid a respective first set of the signals acquired from each of the electrodes while classifying as invalid a respective second set of the signals acquired by each of the electrodes.

9. A method for electrophysiological measurement, comprising:
    inserting into a body cavity of a living subject a probe having a distal end comprising an array of electrodes that are disposed along the distal end and are configured to contact tissue at multiple locations within the body cavity;
    acquiring signals from the electrodes within the body cavity over a period of time during which the probe moves within the body cavity;
    computing, in response the signals, metrics that are indicative of a respective quality of contact between each of the electrodes and the tissue over the period of time, each respective quality of contact being a quantitative indicator of a degree of stable electrical contact between each of the electrodes and the tissue; and
    outputting an indication of the metrics to a user of the system,
    wherein the metrics are indicative of a respective duration during which each of the electrodes was in contact with the tissue in the body cavity over the period of time,
    wherein the signals are indicative of an electrophysiological activity within the tissue, and wherein computing the metrics comprises distinguishing between local signals acquired by the electrodes that are in contact with the tissue and far-field signals acquired by the electrodes that are not in contact with the tissue, and finding the duration during which each of the electrodes is in contact with the tissue in response a relation between the local and far-field signals acquired by each of the electrodes over the period of time.

10. The method according to claim 9, wherein the probe comprises a catheter, and wherein acquiring the signals comprises moving the distal end of the catheter within a chamber of a heart of the subject.

11. The method according to claim 9, wherein the distal end of the probe comprises a flexible structure on which the electrodes are arrayed, and the metrics are indicative of a contact between different parts of the flexible structure and the tissue.

12. The method according to claim 11, wherein the structure comprises multiple flexible spines along which the electrodes are disposed.

13. The method accordingly to claim 9, wherein outputting the indication comprises rendering to a display a graphical icon representing the distal end and incorporating in the graphical icon visual indications of the metrics at respective locations of the electrodes on the distal end.

14. The method according to claim 13, wherein the metrics are represented by color-coding of the respective locations of the electrodes on the graphical icon.

15. The method according to claim 9, wherein the metrics are indicative of a number of valid signals acquired by each of the electrodes from the tissue over the period of time.

16. The method according to claim 15, wherein computing the metrics comprises applying one or more filtering criteria to the signals in order to classify as valid a respective first set of the signals acquired from each of the electrodes while classifying as invalid a respective second set of the signals acquired by each of the electrodes.

\* \* \* \* \*